United States Patent
Sherman

[11] Patent Number: 6,159,933
[45] Date of Patent: Dec. 12, 2000

[54] EMULSION PRECONCENTRATE COMPRISING A CYCLOSPORIN, PROPYLENE CARBONATE, AND GLYCERIDES

[76] Inventor: Bernard Charles Sherman, 50 Old Colony Road, Willowdale, Ontario, Canada, M2L 2K1

[21] Appl. No.: 09/066,712

[22] Filed: Apr. 27, 1998

[51] Int. Cl.⁷ .................................................. A61K 38/00
[52] U.S. Cl. ............................... 514/11; 514/2; 514/885; 424/451; 424/455; 252/302; 252/306; 252/312
[58] Field of Search ..................... 424/451, 455; 514/885, 2, 12, 11; 252/302, 306, 312

[56] References Cited

U.S. PATENT DOCUMENTS 4,388,307  6/1983  Cavanak ................................. 424/177
5,342,625  8/1994  Hauer et al. ........................... 424/455

FOREIGN PATENT DOCUMENTS

| | | | |
|---|---|---|---|
| 2072509 | 12/1992 | Canada | A61K 38/13 |
| 280689 | 8/1997 | New Zealand | A61K 38/13 |
| 2270842 | 3/1994 | United Kingdom | A61K 37/02 |
| 15210 | 10/1991 | WIPO . | |
| WO 94/25068 | 11/1994 | WIPO | A61K 47/10 |
| WO97/36610 | 5/1997 | WIPO | A61K 38/13 |

*Primary Examiner*—F. T. Moezie
*Attorney, Agent, or Firm*—Nixon & Vanderhye P.C.

[57] ABSTRACT

Pharmaceutical compositions in the form of an emulsion preconcentrate or microemulsion preconcentrate which comprise a cyclosporin as active ingredient, propylene carbonate as hydrophilic solvent, glycerides as lipophilic solvent, and a surfactant.

9 Claims, No Drawings

EMULSION PRECONCENTRATE COMPRISING A CYCLOSPORIN, PROPYLENE CARBONATE, AND GLYCERIDES

TECHNICAL FIELD

The invention is directed to pharmaceutical compositions which facilitate the administration of cyclosporins.

BACKGROUND ART

The term "solvent system" as used herein refers to a carrier in which an active drug (i.e. a cyclosporin) is dissolved. The solvent system may be a single solvent or a mixture of ingredients included as solvents, surfactants, diluents, or for other purposes.

The term "cyclosporin" as used herein refers to any member of a class of nonpolar polypeptides, as defined in the Merck Index, Twelfth Edition. One such cyclosporin is cyclosporin A, also known as "cyclosporine" and hereinafter referred to as "cyclosporine", known to be therapeutically active as an immunosuppressant.

Cyclosporins are hydrophobic and have low solubility in aqueous media. This makes it difficult to design pharmaceutical compositions (i.e. dosage forms) comprising cyclosporins which exhibit satisfactory absorption into systemic circulation after oral administration, or absorption into the target tissue upon topical administration.

The cyclosporin can be dissolved in an organic solvent (e.g. ethanol or propylene glycol), but if the solvent is water-miscible, when the composition is mixed with gastrointestinal fluid or other aqueous medium, the cyclosporin will precipitate.

Methods of overcoming this problem are now known in the prior art. The most common approach is to dissolve the cyclosporin in a solvent system that comprises at least one lipophilic (hydrophobic) solvent and a surfactant, so that the composition disperses into an emulsion when mixed into gastrointestinal fluid or other aqueous medium.

Such compositions are called "emulsion preconcentrates".

U.S. Pat. No. 4,388,307 discloses such compositions. A commercial product that has been sold under the trademark "Sandimmune" is made according to U.S. Pat. No. 4,388,307, and, more specifically, comprises cyclosporine dissolved in a solvent system comprising ethanol as hydrophilic solvent, a vegetable oil as lipophilic solvent, and a surfactant. The ethanol is required to dissolve the cyclosporin in the composition as the vegetable oil has inadequate capacity to dissolve cyclosporins. While this composition is superior to previously known compositions, it still exhibits absorption that is less than the maximum possible and is variable. Moreover, the use of ethanol has disadvantages, as ethanol is volatile, and Sandimmune capsules must be individually packaged in metallic pouches to avoid evaporation of the ethanol.

U.S. Pat. No. 5,342,625 discloses compositions that are superior in certain respects to the compositions taught in the prior reference. The compositions of U.S. Pat. No. 5,342,625 also comprise, in addition to the cyclosporin, a hydrophilic solvent, a lipophilic (i.e. hydrophobic) solvent and a surfactant. Again, the hydrophilic solvent is an alcohol and more particularly a polyol which consists of either propylene glycol or a pharmaceutically acceptable alkyl or tetrahydrofurfuryl di- or partial-ether of a low molecular weight mono- or poly-oxy-alkanediol. This reference teaches that only lipophilic solvent that is not miscible with the selected hydrophilic solvent is suitable for the purpose of this invention.

It is also disclosed that compositions according to U.S. Pat. No. 5,342,625, when added to water, disperse into emulsions with droplet size of less than 2000 Å, which is smaller than obtained with prior art compositions, thus leading to improved absorption.

Emulsions with droplet size of less than 2000 Å are defined as "microemulsions". Compositions that, upon addition to water, disperse into microemulsions are called "microemulsion preconcentrates".

UK Patent Application No. 2 270 842 published Mar. 30, 1994 relates to pharmaceutical compositions comprising cyclosporin in a carrier medium; the carrier comprises:

(i) a hydrophilic organic solvent in the form of a polyol and/or a lower alkanol such as propylene glycol and ethanol;

(ii) a lipophilic solvent; and (iii) a polyoxyethylene-sorbitan-fatty acid ester surfactant.

Canadian Patent 2072509 discloses microemulsion preconcentrates comprising a cyclosporin dissolved in a carrier which comprises:

(i) as hydrophilic solvent, propylene glycol, either alone or with other lower alkanols e.g. ethanol;

(ii) as lipophilic solvent a mixed mono-, di- and triglyceride; and (iii) a surfactant.

Again the hydrophilic solvent and the lipophilic solvent are not intermiscible.

The compositions taught by Canadian Patent 2072509 appear to be within the scope of claim 1 of U.S. Pat. No. 5,342,625, but limited to propylene glycol as hydrophilic solvent and a mixed mono-, di- and tri-glyceride as lipophilic solvent.

A composition made according to the disclosure of Canadian patent 2072509 is now marketed under the trademark "Neoral", in the form of both an oral liquid which is a microemulsion preconcentrate intended to be diluted into an aqueous drink before ingestion, and a soft gelatin capsule containing the microemulsion preconcentrate.

For both the soft gelatin capsules and the oral liquid, the labelling indicates that the "Neoral" emulsion preconcentrate comprises cyclosporine dissolved in ethanol and propylene glycol as hydrophilic solvents, corn oil glycerides as lipophilic (hydrophobic) solvent, and polyoxyl 40 hydrogenated castor oil as surfactant. It also contains dl-alpha-tocopherol at a level of about one percent by weight as antioxidant. Although Canadian patent 2072509 includes some examples without ethanol, the use of ethanol in the commercial "Neoral" product indicates that compositions without ethanol either were not found to give adequate stability or were not found to give adequate absorption upon ingestion.

While Neoral does enable improved absorption relative to Sandimmune, it still has certain undesirable properties. Specifically:

1. Ethanol is volatile, so that the soft gelatin capsules have to be packaged individually in metallic pouches to prevent evaporation of the ethanol.

2. Ethanol contributes to an undesirable taste of the microemulsion preconcentrate, so that, even after dilution into a sweetened drink, there is still a somewhat unpleasant taste.

3. The lipophilic solvent, which is mixed mono- di- and tri-glycerides, is relatively expensive.

Several prior art publications disclose further improvements achieved by selecting different lipophilic and/or hydrophilic solvents.

International Publication Number WO94/25068 discloses improved compositions in the form of microemulsion preconcentrates in which the principal solvent for the cyclosporin is an alcohol which is selected from alcohols having a boiling point above 100° C. and a solubility in water of under 10 g per 100 g at 20° C. Because such alcohols are good solvents for cyclosporine, they eliminate the need for ethanol. Preferred alcohols, within the scope of the disclosure of WO94/25068, are saturated alkyl alcohols having 8 to 14 carbon atoms per molecule, including 1-octyl, 2-octyl, 1-decyl, 1-dodecyl and 1-tetradecyl alcohols. However, a problem with such compositions is that the selected alcohols are more toxic than other lipophilic solvents generally used in the art.

New Zealand Patent Application No. 280689 discloses improved microemulsion preconcentrates in which a cyclosporin is dissolved in a solvent system comprising a lipophilic (hydrophobic solvent), a hydrophilic solvent and a surfactant, wherein the lipophilic solvent is selected from tocol, tocopherols and tocotrienols, and derivatives thereof, including specifically Vitamin E.

New Zealand Patent Application No. 280689 also discloses use of propylene carbonate as hydrophilic solvent to overcome some of the problems found in the prior art compositions.

Preferred compositions within the scope of New Zealand Patent application No. 280689 comprise both a lipophilic solvent selected from tocol, tocopherols and tocotrienols and derivatives thereof, including specifically Vitamin E, and a hydrophilic solvent selected from propylene carbonate and polyethylene glycols having average molecular weight of less than 1000. In the compositions disclosed in New Zealand Patent application No. 280689, the lipophilic and hydrophilic solvents are again not intermiscible. While these compositions exhibit improved properties over the prior art, the disclosed lipophilic solvent such as Vitamin E are relatively expensive.

Accordingly, it is an object of the within invention to enable galenical formulations comprising cyclosporin which exhibit improved properties or at least perform as well as the ones taught by New Zealand Patent Application No. 280689 and which are less expensive, thus reducing the cost of therapy.

SUMMARY OF THE INVENTION

It has been surprisingly found that when propylene carbonate is used as hydrophilic solvent, excellent emulsion preconcentrate and microemulsion preconcentrates can be made using relatively inexpensive glycerides as lipophilic solvent, and without use of ethanol.

The present invention thus provides a pharmaceutical composition in the form of an emulsion preconcentrate (or microemulsion preconcentrate) comprising a cyclosporin dissolved in a solvent system comprising propylene carbonate as hydrophilic solvent, a lipophilic solvent selected from glycerides, and at least one surfactant.

Surprisingly, contrary to the teaching of the prior art, satisfactory formulations are obtained even using as lipophilic solvent glycerides that are miscible with propylene carbonate, and despite the fact that propylene carbonate is not an alcohol or a polyol.

DETAILED DESCRIPTION OF THE INVENTION

As aforesaid, compositions within the scope of the present invention will comprise a cyclosporin, propylene carbonate, glycerides, and a surfactant.

For purposes of the within specification and claims, the term "glycerides" is to be understood to include mono-, di-, and tri-esters of glycerol with fatty acids, and mixtures thereof.

"Fatty acids" will be understood to include both medium chain (e.g. $C_8$–$C_{10}$) fatty acids and long chain (e.g. $C_{12}$–$C_{18}$) fatty acids, both unsaturated and saturated.

It will be understood that an unreacted glycerol molecule has three hydroxyl moeities. Monoglyceride will have two unreacted hydroxyls, diglycerides will have one, and triglycerides will have none.

Hence, mono- and di-glycerides formed by glycerol and fatty acids are capable of further esterification at the remaining one or two hydroxyls.

For the purposes of the within specification and claims, the term "glycerides" is to be understood to include compounds formed by further esterification of fatty acid mono- and di-glycerides with acids other than fatty acids.

This will include, for example, acetylated monoglycerides which are formed by reacting fats with glycerol and triacetin.

Glycerides useable within the scope of the invention will thus include, but not be limited to, the following:

i) vegetable oils (which are comprised primarily of fatty acid triglyercides), and extracts therefrom.

ii) any of the mono- or diglycerides approved for pharmaceutical use, including, for example, glyceryl monooleate.

iii) a mixed mono-, di-, and triglyceride, which will preferably comprise a mixture of $C_{12\text{-}20}$ fatty acid mono-, di- and triglycerides.

Preferably these mixed glycerides are predominantly comprised of unsaturated fatty acid residues, in particular $C_{18}$ unsaturated fatty acid residues such as linolenic, linoleic and oleic acid residues.

The mixed mono-, di-, and tri-glycerides are preferably predominantly comprised of mono- and di-glycerides.

The mixed mono-, di-, and tri-glycerides may be prepared by admixing individual mono-, di, and tri-glycerides in appropriate relative proportions. Conveniently, however, the mixed glycerides comprise transesterification products of vegetable oils, for example almond oil, ground nut oil, olive oil, peach oil, palm oil, soybean oil, corn oil, sunflower oil or safflower oil, with glycerol. Preferably the vegetable oil is corn oil. Also, mixtures of the oils may be transesterified with glycerol.

The transesterification products are generally obtained by heating the selected vegetable oil with glycerol to effect transesterification or glycerolysis. This may be carried out at high temperature in the presence of an appropriate catalyst, under an inert atmosphere and with continuous agitation. In addition to the mono-, di- and tri-glyceride components, the transesterification products also generally comprise minor amounts of free glycerol.

Transesterification products of corn oil and glycerol provide particularly suitable mixed mono-, di-, and tri-glycerides. An example of a suitable mixed glyceride product is the transesterification product commercially available under the trade name MAISINE (available from the company Etablissements Gattefosse, of 36 Chemin de Genas, P.O. Box 603, 69804 Saint-Priest, Cedex (France)). This product is comprised predominantly of linoleic and oleic acid mono-, di- and triglycerides together with minor amounts of palmitic and stearic acid mono-, di- and tri-glycerides.

iv) Acetylated monoglycerides which consist of glycerol esterified with fatty acids at one of the three hydroxyl functions, with the other two hydroxyls replaced by an acetyl moeities.

Acetylated monoglycerides are sold in the United States under the tradename "Myvacet" by Eastman Chemical Products Inc. They are made by reacting fats with glycerine and triacetin.

By adjusting the degree of saturation of the monoglyceride and the degree of acetylation, different characteristics are obtained.

Fully acetylated monoglycerides prepared from unsaturated monoglycerides are liquids at room temperature. In this context, the phrase "fully acetylated" is intended to mean having a minimum acetylation of about 96%.

Fully acetylated monoglycerides are currently available from Eastman Chemical Products Inc. under the designations Myvacet 9-08 and Myvacet 9-45. For Myvacet 9-08, the fat source is hydrogenated coconut oil. For Myvacet 9-45 the fat source is partially hydrogenated soybean oil.

Myvacet 9-08 and Myvacet 9-45 are both liquids at room temperature, having melting points of 4° C. to 12° C. Both are well suited for use as lipophilic solvent, but Myvacet 9-45 is especially preferred because of its lower cost.

The preferred glycerides are mixed mono-, di- and tri-glycerides and acetylated monoglycerides. Most preferred is acetylated monoglycerides because of the following advantages:

1. Low cost.
2. They are good solvents for cyclosporins.
3. They are entirely miscible with propylene carbonate.

The fact that a microemulsion preconcentrate can be made using acetylated monoglyceride as lipophilic solvent and propylene carbonate as hydrophilic solvent, despite the fact that they are miscible with each other, is contrary to the teaching of U.S. Pat. No. 5,342,625.

The compositions of the present invention will also include at least one surfactant, by which is meant a compound with both lipophilic and hydrophilic properties, which improves the dispersibility of the composition into an emulsion or microemulsion in water.

Suitable surfactants include those cited in U.S. Pat. No. 5,342,625 and Canadian patent 2072509.

Preferred surfactants are polyoxyethylene glycolated natural or hydrogenated vegetable oils; for example, polyoxyethylene glycolated natural or hydrogenated castor oil. Particularly preferred is the surfactant designated in the United States Pharmacopoeia and National Formulary as Polyoxyl 40 Hydrogenated Castor Oil, which is available under the tradename "Cremophor RH40".

It has been surprisingly found that these preferred surfactants act synergistically with other surfactants, so that inclusion of a second surfactant as co-surfactant can reduce the total amount of surfactant needed, without loss of effectiveness in enabling dispersion into an emulsion or microemulsion.

Preferred surfactants for use as co-surfactant are polyoxyethylene-sorbitan-fatty acid esters; e.g. mono- and tri-lauryl, palmityl, stearyl and oleyl esters; e.g. products of the type known as polysorbates and available under the tradename "Tween". Especially preferred as co-surfactant is polyoxyethylene 20 sorbitan monolaurate, which is also known as polysorbate 20.

Compositions in accordance with the invention may also contain other ingredients.

For example, the composition may include, in addition to the foregoing, one or more other ingredients that are included as diluents, thickening agents, antioxidants, flavouring agents, and so forth.

Compositions in accordance with the invention may be liquids at ambient temperature or they may be solids prepared, for example, by use of one or more ingredients with melting point above ambient temperature. The ingredients may be blended at a temperature above the melting point and then used to fill capsules while still molten, or cooled to form solids. The solids may be ground into granules or powder for further processing; for example, filling capsules or manufacture of tablets.

If it is desired to increase the melting point to ensure that the composition is a solid at room temperature, this may be accomplished by adding a further ingredient with a relatively high melting point, such as, for example, polyethylene glycol with average molecular weight of above 1000.

Capsules or tablets may be further process by applying coatings thereto.

Compositions in accordance with the invention may comprise dosage forms for direct administration as emulsion preconcentrates or microemulsion preconcentrates. For example, an emulsion preconcentrate or microemulsion preconcentrate may be directly used as liquid for oral ingestion, parenteral use, or topical application or it may be encapsulated into gelatin capsules for oral ingestion.

However, the present invention also provides pharmaceutical compositions in which the emulsion preconcentrate or microemulsion preconcentrate is further processed into an emulsion or a microemulsion. Thus where oral administration is practised, emulsions or microemulsions obtained, e.g. by diluting a preconcentrate with water or other aqueous medium (for example, a sweetened or flavoured preparation for drinking), may be employed as formulations for drinking. Similarly, where topical application is intended, compositions comprising an emulsion preconcentrate, a thickening agent, and water will provide an aqueous emulsion in gel, paste, cream or like form.

Compositions in accordance with the present invention, whether emulsion preconcentrates, microemulsion preconcentrates, emulsions, or microemulsions, may be employed for administration in any appropriate manner and form; e.g. orally, parenterally, topically; or rectally.

The relative proportion of the cyclosporin and other ingredients in the compositions of the invention will, of course, vary considerably depending on the particular type of composition concerned; e.g. whether it is an emulsion preconcentrate, microemulsion preconcentrate, emulsion, or microemulsion, the route of administration, and so forth. The relative proportions will also vary depending on the particular ingredients employed and the desired physical characteristics of the composition; e.g. in the case of a composition for topical use, whether this is to be a free flowing liquid or a paste. Determination of workable proportions in any particular instance will generally be within the capability of persons skilled in the art.

The invention will be more fully understood by the following examples which are illustrative but not limiting of compositions in accordance with the present invention.

EXAMPLES

In each of the following examples, the ingredients were weighed into a test tube in the proportions shown, the test tubes and contents were warmed to 100° C. in a water bath, and then the test tubes were shaken until the contents of each tube were interdissolved to form a clear solution.

Then 1 g from the resulting emulsion preconcentrate in each test tube was transferred to another test tube, about 20 mL of warm (37° C.) water was added, and the test tube was shaken to disperse the 1 g of the composition in the water to form an emulsion or microemulsion. The resultant emulsions or microemulsions were then compared for clarity by measuring the light transmittance through a 1 cm cell at 600 nm. A higher transmittance indicates a smaller droplet size and hence, a finer emulsion or microemulsion.

| Example No.: | 1 | 2 | 3 | 4 |
|---|---|---|---|---|
| Cyclosporine | 1.0 | 1.0 | 1.0 | 1.0 |
| Maisine | 3.2 | 2.8 | 2.4 | 2.0 |
| Propylene Carbonate | 1.4 | 1.4 | 1.4 | 1.4 |
| Cremophor RH40 | 3.8 | 3.8 | 3.8 | 3.8 |
| Polysorbate 20 | 1.2 | 1.6 | 2.0 | 2.4 |
| Total: | 10.6 | 10.6 | 10.6 | 10.6 |
| Percent Transmittance at 600 nm | 83.9 | 91.1 | 92.5 | 94.4 |
| Example No. | 5 | 6 | 7 | 8 |
| Cyclosporine | 1.0 | 1.0 | 1.0 | 1.0 |
| Myvacet 9–45 | 2.7 | 2.5 | 2.3 | 2.1 |
| Propylene Carbonate | 1.6 | 1.6 | 1.6 | 1.6 |
| Cremophor RH40 | 3.6 | 3.6 | 3.6 | 3.6 |
| Polysorbate 20 | 1.8 | 2.0 | 2.2 | 2.4 |
| Total: | 10.7 | 10.7 | 10.7 | 10.7 |
| Percent Transmittance at 600 nm | 87.5 | 89.4 | 91.6 | 91.4 |

As aforesaid, the transmittance is that of an emulsion or microemulsion made by dispersing 1 g of the composition in about 20 mL of warm (37° C.) water.

In each case, the density of the preconcentrate was about 1.06 to 1.07 g/mL, so that each mL of the preconcentrate contained about 100 mg of cyclosporine.

As a basis for comparison, 1 g of the marketed product, Neoral Oral Solution, was similarly dispersed in about 20 mL of warm (37° C.) water and the transmittance through 1 cm cell at 600 nm was measured to be 83.9%. The compositions of all of examples 1 to 8 thus all gave higher transmittance than Neoral, which indicates that the microemulsions are at least as fine as obtained with Neoral.

What is claimed is:

1. A pharmaceutical composition, wherein said composition is an emulsion preconcentrate, comprising a cyclosporin dissolved in a solvent system comprising propylene carbonate, a lipophilic solvent selected from glycerides, and at least one surfactant.

2. A composition as in claim 1 wherein said composition is a microemulsion preconcentrate.

3. A composition as in claim 1 wherein the lipophilic solvent is mixed mono-, di, and tri-glyceride.

4. A composition as in claim 1 wherein the lipophilic solvent is miscible with propylene carbonate.

5. A composition as in claim 4 wherein the lipophilic solvent is an acetylated monoglyceride.

6. A composition as in claim 1 wherein the surfactant is polyoxyethylene glycolated natural or hydrogenated vegetable oil.

7. A composition as in claim 6 wherein the surfactant is polyoxyl 40 hydrogenated castor oil.

8. A composition as in claim 1 wherein the surfactant is a polyoxyethylene-sorbitan-fatty acid ester.

9. A composition as in claim 1 comprising two surfactants, one of which is a polyoxyethylene glycolated natural or hydrogenated vegetable oil and the second of which is a polyoxyethylene-sorbitan-fatty acid ester.

* * * * *